US00PP09350P

United States Patent [19]

Lemon

[11] Patent Number: Plant 9,350

[45] Date of Patent: Oct. 31, 1995

[54] FLORIBUNDA GERANIUM 'KATHERINE'

[75] Inventor: David Lemon, Lompoc, Calif.

[73] Assignee: John Bodger & Sons Company, South El Monte, Calif.

[21] Appl. No.: 281,737

[22] Filed: Jul. 27, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Fulwider, Patton, Lee & Utecht

[57] ABSTRACT

The cultivar is characterized by its bright white color. Its compact, controlled growth habit and prolific blooms provide for superb cuttings and performs equally well in hanging baskets or in a ground bed. The blooms are heat tolerant.

1 Drawing Sheet

BACKGROUND OF THE NEW PLANT

The present invention comprises a new and distinct cultivar of *Pelargonium×hortorum* known by the varietal name Katherine (Oglevee No. 9042, Bodger No. 9GM 65-7). The new variety was discovered in a selective breeding program by David Lemon at Bodger Seeds, Ltd., Lompoc, Calif. The new variety is a selection from the crossing of Bodger No. 8GM 262-5×7GM 265-2.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° fahrenheit night temperature, 68° fahrenheit day temperature, 72° fahrenheit vent temperature and grown in a soilless media of constant fertilizer 200 to 250 parts per million of nitrogen and potassium has a response time of six weeks from the rooted cutting to a flowering plant in a 10.0 cm pot.

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories where taken on rooted cuttings potted on Feb. 9, 1993 and flowered Mar. 9, 1993 under full light and greenhouse, and colorings were taken indoors under 200–220 foot candles of fluorescent cool white light using The R.H.S. Colour Chart of The Royal Horticultural Society of London.

THE PLANT

Classification:

*Botanical.*—*Pelargonium×hortorum.*

Form: Semi-dwarf, compact, free basal branching; lateral and cascading growth; neat formal plant habit.

*Height.*—16.0–17.0 cm from the media surface.

*Growth.*—Lateral and procumbent habit; free basal branching.

*Strenght.*—Free and early flowering, free standing, multipurpose uses.

Foliage: Light zone present, stalked leaf attachment.

Leaves:

*Size.*—5.0–8.0 cm across.

*Shape.*—Reniform; cordate base.

*Margin.*—Crenate.

*Texture.*—Pubescent; dull.

*Color.*—Top; Green Group 137B. Bottom: Yellow/green Group 146B.

*Ribs and veins.*—Palmate venation; Color: Yellow/Green group 147D.

Petioles:

*Length.*—5.0–9.0 cm.

*Color.*—Yellow/green group 146B.

Stem:

*Color.*—Yellow/green group 146C.

*Internodes.*—2.0–2.5 cm in length.

THE BUD

Shape: Upright; hemispherical cluster.

Size: 1.5–2.5 cm across.

INFLORESCENCE

Blooming habit: Upright, continuous, very floriferous.

Size: 6.5–7.5 cm across.

Borne: Floret on pedicel; pedicel on peduncle; 5.0–10.0 cm above foliage.

Florets:

*Form.*—Flat to slightly cupped.

*Color.*—Top: White group 155D. Bottom: White group 155D.

*Petals.*—12–15 in number; separate, not united; margin entire; obovate; slightly cupped.

*Size.*—3.0–4.0 cm across.

*Texture and appearance.*—Smooth, appearance from a distance is clean bright white flower above medium green foliage.

Petaloids:

*Quantity.*—1 to 5.

*Shape.*—Narrow, elongated, twisted, some tubular.

*Color.*—White group 155D.

Pedicel:

*Length.*—1.5–2.5 cm.

*Color.*—Yellow/green group 146C.

Peduncle: Arises from node opposite leaf petiole.

*Length.*—12.0–17.0 cm in length.

*Color.*—Yellow/green group 146B.

Persistence:

*Disease resistance.*—Not known.

*Lasting quality.*—Continuous blooming, heat tolerant.

REPRODUCTIVE ORGANS

Stamens:

*Anthers.*—2.0 mm in length.

*Filaments.*—5.0–10.0 mm in length; white.

*Pollen.*—Golden Brown.

Pistils:

*Number*—One.

*Length.*—7.0–8.0 mm.

*Stigma.*—One; 5–6 parted.

*Style.*—2.0–3.0 mm, white to pale green in color.

Ovaries: Superior, very pubescent; pale green in color, 5.0–6.0 mm in length, 1.0–2.0 mm across.

Fruit: Occasinal fruit noted.

GENERAL CHARACTERISTICS

This new geranium variety, Katherine, is an expansion on the current floribunda varieties. The new flower color, white, adds to the current group of light pink, pink, salmon and red floribundas. The plant form is very controlled in a neat mound habit. For production purposes, Katherine is a very good cutting producer. Katherine can be used in either having baskets or ground beds and will be a very prolific bloomer. Many white flower clusters create a large continuous bouquet.

I claim:

1. A new and distinct variety of geranium plant, substantially as shown and described.

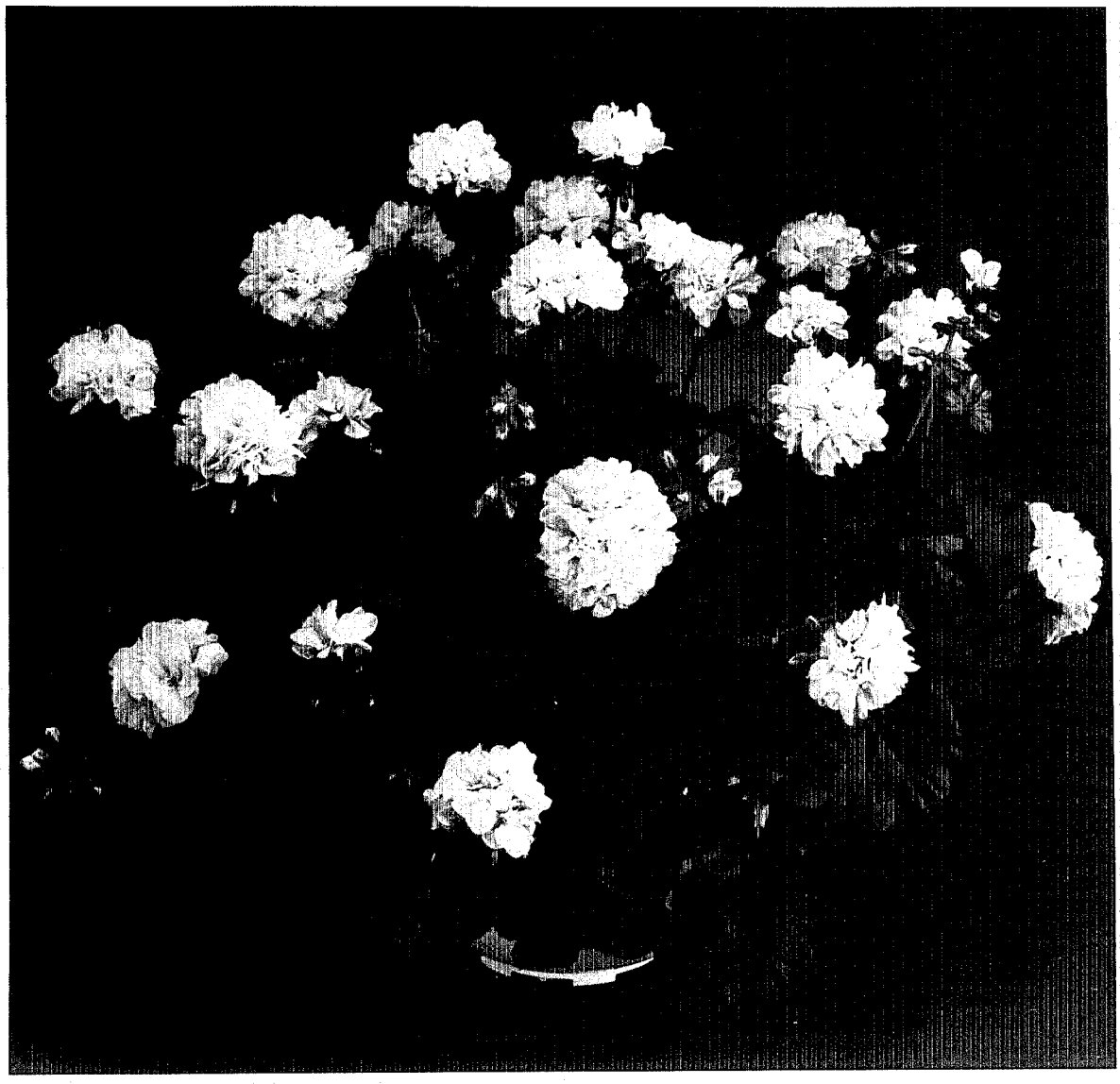

* * * * *